United States Patent [19]

Seiderman

[11] Patent Number: 4,767,401
[45] Date of Patent: Aug. 30, 1988

[54] IONTOPHORETIC ADMINISTRATION OF IONIZABLE OR POLAR MEDICAMENTS TO A MAMMALIAN BODY

[76] Inventor: Maurice Seiderman, 3306 Deronda Dr., Hollywood, Calif. 90068

[21] Appl. No.: 411,657

[22] Filed: Aug. 26, 1982

Related U.S. Application Data

[63] Continuation of Ser. No. 128,715, Mar. 10, 1980, abandoned, which is a continuation of Ser. No. 006,363, Jan. 25, 1979, abandoned, which is a continuation of Ser. No. 896,435, Apr. 14, 1978, abandoned, which is a continuation of Ser. No. 758,774, Jan. 12, 1977, abandoned, which is a continuation-in-part of Ser. No. 570,384, Apr. 22, 1975.

[51] Int. Cl.$^4$ .............................................. A61N 1/30
[52] U.S. Cl. ...................................... 604/20; 128/803
[58] Field of Search ................. 128/82.1, 419 R, 803; 604/20

[56] References Cited

U.S. PATENT DOCUMENTS

| | | | |
|---|---|---|---|
| 588,479 | 8/1897 | Roedel | 604/20 |
| 679,239 | 7/1901 | Mossberg | 604/20 |
| 1,967,927 | 7/1934 | Deutsch | 604/20 |
| 2,202,566 | 5/1940 | Schulte | 128/156 X |
| 2,493,155 | 1/1950 | McMillan | 604/20 |
| 2,887,112 | 5/1959 | Smith | 128/644 |
| 3,215,139 | 11/1965 | Dietz | 604/20 |
| 3,520,297 | 7/1970 | Bechtold | 604/20 |
| 3,563,228 | 2/1971 | Seiderman | 128/82.1 |
| 3,742,955 | 7/1973 | Battista et al. | 128/DIG. 8 |
| 3,799,162 | 3/1974 | Romero-Sierra | 604/20 |
| 3,810,473 | 5/1974 | Cruz et al. | 128/334 R |
| 3,875,937 | 4/1975 | Schmitt et al. | 128/156 |
| 3,929,131 | 12/1975 | Hardwick | 128/82.1 X |
| 3,964,477 | 6/1976 | Ellis et al. | 604/20 |
| 4,019,510 | 4/1977 | Ellis | 604/20 |

FOREIGN PATENT DOCUMENTS 2217689  10/1972  Fed. Rep. of Germany ........ 604/20

Primary Examiner—Lee S. Cohen
Attorney, Agent, or Firm—Burns, Doane, Swecker & Mathis

[57] ABSTRACT

A method for the iontophoretic administration of topical or systemic ionizable or polar medicaments to a mammalian body, and articles adapted therefor, are disclosed.

22 Claims, 1 Drawing Sheet

IONTOPHORETIC ADMINISTRATION OF IONIZABLE OR POLAR MEDICAMENTS TO A MAMMALIAN BODY

CROSS REFERENCE TO RELATED APPLICATION

This application is a continuation of application Ser. No. 128,715, filed Mar. 10, 1980, now abandoned, which is in turn a continuation of Ser. No. 6,363, filed Jan. 25, 1979, now abandoned, which is in turn a continuation of Ser. No. 896,435, filed Apr. 14, 1978, now abandoned, which is in turn a continuation of Ser. No. 758,774, filed Jan. 12, 1977, now abandoned which is in turn a continuation-in-part of Ser. No. 570,384, filed Apr. 22, 1975.

BACKGROUND OF THE INVENTION

1. Field of the Invention

The present invention relates generally to the iontophoretic administration of topical or systemic ionizable or polar medicaments to a mammalian body, which medicaments are responsive to an electric field, and, more especially, to the administration of denatured or undenatured proteins, with or without a metallic component, to a wound, lesion, or the like, under the influence of an electric field. The invention also relates to articles adapted for use in practicing the present method.

2. Description of the Prior Art

There is a recognized need to provide protection for a wound, lesion, or the like, on an animal body during the healing thereof. My co-pending application Ser. No. 570,384, as well as my earlier U.S. Pat. No. 3,563,228, are devoted to furnishing methods and articles to this end. Specifically, these earlier works have provided, as a common thread, the ability to form an adherent, skin-like collagen membrane over such damaged areas in order to minimize contamination of the wound with, for example, infectious or other foreign materials, while alleviating pain and loss of body fluids during the healing process. Fundamentally, collagen is caused to form a biological junction with damaged collagen fibrils at the wound site under the influence of an applied electric field.

The utility of an electric field in medical treatment is, of course, well known. For example, it has been commonplace to provide bandage-like articles with electrodes comprised of dissimilar metallic materials to create a galvanic cell for various types of clinical treatment. These articles, conventionally termed voltaic plasters, have been devised for the iontophoretic administration of certain medicaments through a patient's skin. Note, for example, U.S. Pat. Nos. 116,562, 175,974, 222,276, 393,741, and 1,967,927.

The prior art voltaic plasters suffer numerous, significant disadvantages, however. Perhaps the most important is the tendency for electrode burns due to the materials employed, chiefly based upon copper and zinc as the dissimilar materials for the galvanic cell. Also, the efficacy of the prior art devices in terms of the ability to effectively deliver a medicament has led to their desuetude.

Currently, when it is desired to iontophoretically administer topical medicaments, external power sources are employed. Note, e.g., U.S. Pat. No. 3,163,166, as well as my earlier U.S. Pat. No. 3,563,228.

Because of the prior art inability to effectively deliver medicaments, notwithstanding deleterious side-effects from the very nature of the galvanic cell construction from dissimilar active metals, and further in light of the undesirability of employing an external power source, the need exists to provide improved voltaic plasters which are extremely efficient in the delivery of medicaments, and which do not suffer the problems of, e.g., electrode burns. Additionally, the need exists for such delivery devices which are simple, but efficient, both in terms of construction and individual use by the consuming public. Moreover, the need exists to provide an iontophoretic delivery system for a broad range of ionizable or polar medicaments not, hitherto, employed to these ends.

SUMMARY OF THE INVENTION

In accordance with the deficiencies of the prior art, it is a major object of the present invention to provide an improved method for the iontophoretic administration of an ionizable or polar medicament to a mammalian body.

It is also an object of the present invention to provide an article for the iontophoretic administration of an ionizable or polar medicament to a mammalian body.

Yet a further object of the present invention is to provide a bandage-like article capable of generating a slight electric current and concomitant electric field when applied to a mammalian body in order to effect the iontophoretic administration of ionizable or polar medicaments thereto, without resulting in electrode burning of the body.

Still a further object of the present invention is to provide for the iontophoretic administration of proteinaceous medicaments, wherein the protein component is either denatured or undenatured, with or without a metallic component.

Yet other objects of the present invention will become apparent to the skilled artisan upon review of the detailed description of the present invention and exemplary embodiments disclosed therein.

Surprisingly, it has been determined that the foregoing objects of the present invention may be realized, whereby an ionizable or polar medicament may be effectively administered to a mammalian body, when there is provided an iontophoretic impetus derived, in part, from naturally-occurring local charges on the body to be treated in concert with a compatible electrode borne upon or comprising a bandage or bandage-like substrate. The instant method is efficacious for the administration of any ionizable or polar medicament responsive to an electric field; proteinaceous medicaments, or derivatives thereof, being preferred. The proteinaceous medicaments may be either undenatured or denatured, e.g., the protein component of mild or strong silver protein, alginates, and the like. Additionally, there may be present various metallic salts or compounds, particularly when a denatured protein is employed. That metallic ion most preferred is silver, albeit other medicinally-effective metallic ions may be incorporated.

The bandage or bandage-like device employed to deliver the medicament to the mammalian body has an integral electrode of, e.g., foil in electrically-cooperative relationship with the medicament thereon. Aluminum is the most preferred electrode material; however, the electrode might be fabricated from any of a number of known active materials.

When the device, comprised of the electrode and medicament, is applied to a mammalian body, natural body fluids or, optionally, administered isotonic or other electrolytic fluids, will establish the appropriate electric current and concomitant field for delivery of the medicament deep within the wound, lesion, or the like, on the body. The medicaments envisioned for use in conjunction with this invention comprise, but are not limited to, anti-infective, analgesic, bacteriostatic, and like ionizable or polar compounds, provided the compound is responsive, in terms of migration, to an electric field.

DETAILED DESCRIPTION OF THE INVENTION

Figure 1:
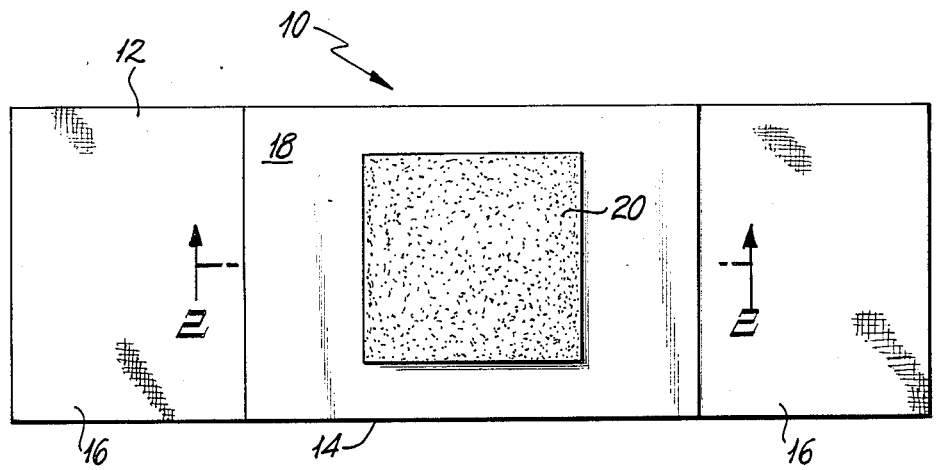
FIG. 1 is a plan view of a bandage for practicing the method of the present invention.

In order to more fully elucidate upon the objects and advantages of the present invention, the following detailed description will be given in terms of various preferred embodiments and exemplified with respect thereto. The same are intended, however, to be illustrative and in no wise limitative.

The present invention pertains, broadly, to methods for the iontophoretic administration of various ionizable or polar medicaments to a mammalian body and a delivery system therefor. More specifically, the present invention is particularly adapted for the administration of various proteinaceous and/or biocompatible metallic medicaments, or derivatives thereof, to a mammalian body from a bandage or bandage-like article under the influence of an electric field established between the bandage and the body.

It is observed that prior art voltaic plasters suffer numerous disadvantages, the most significant being risk of electrode burns to the body being treated due to the construction of the bandage from highly active dissimilar metals as the galvanic electrode materials, and an inability to effectively deliver a wide range of medicinally-effective medicaments. Both of these significant drawbacks are overcome by the present invention, by providing an integral electrode on a bandage substrate having a quantity of medicament also borne thereon. When applied to a mammalian body, natural body fluids or applied isotonic fluids will create a voltaic effect whereby the medicament is caused to migrate deeply within a wound, lesion, or the like, to elecit its desired pharmacologic response.

In part, the improvement derived from the present invention is coupled with the recognition that a mammalian body possesses a slight, inherent negative electric charge, particularly at areas proximate the site of a wound, lesion, or the like. Thus, by appropriate design of a delivery device, materials may be employed which advantageously utilize this electrical characteristic thereby overcoming the need for dissimilar electrodes to effect the galvanic cell while yet providing for the generation of a suitable electric field for the isotophoretic impetus. The improvement in the iontophoretic administration of medicaments in accordance with the present invention lies also, in part, in administering a broad range of ionizable or polar compounds responsive to the applied electric field.

While numerous anionic, cationic, and polar medicaments, including certain amphoteric medicaments, are envisioned within the scope of the present invention, the preferred are proteinaceous medicaments, either undenatured or denatured. Thus, these preferred medicaments include the protein component of mild or strong silver protein, alginates, and the like. Additionally, various effective metallic salts may be employed in the iontophoretic administration method according to the present invention in conjunction with the protein or derivative thereof. It has been determined that the proteinaceous medicament may be employed alone when the protein component is not denatured. When, however, that protein component is denatured, it is particularly beneficial to employ a metallic salt, most preferably a silver salt. However, other medicinally-effective equivalent metallic salts might be utilized. Likewise, other medicaments including, particularly, Dexamethasone Sodium Phosphate, Methylprednisolone Sodium Succinate, Flurandrenolide, and Amphotericin, are preferred compounds for use in conjunction with the present invention. These compounds may be employed individually or in admixture, with or without the additional presence of metallic salts, or denatured or undenatured mild silver proteins. Moreover, various steriods, antibotics, and antifungal compounds may also be employed, together or separately as might be desired. Further medicinally-effective compounds and preparations may be selected from specific pharmocological effects, such selection being within the scope of those skilled in the art.

The most preferred proteinaceous medicament is the aneseptically-effective mild silver protein, which is a colloid of silver with protein, containing on the order of 19 to 25% silver. This material is readily available, commercially; and is described in "The Merck Index", Merck and Co., Inc., 5th Edition, 1940, page 458. However, other anti-infectious, analgesic, bacteriostatic, and like proteinaceous compounds may be employed to this end.

In electrically-cooperative relationship with the medicament is an electrode, which may assume any of a number of physical configurations. Most preferable is a metallic foil, although any electrochemically active material may be utilized and may be deposited in the form of a liquid such as, for example, paint, and subsequently dried. The electrode material should be selected from those known to be compatible with the mammalian body for the obvious reasons including toxicity, irritation, etc. As will become more apparent hereinbelow, a salient distinction between the bandage of the present invention and those of the prior art is the absence of a galvanic couple of active metallic components on the bandage substrate to which has been attributed the significant problem of electrode burns indigenous to the latter. That is, the instant bandage employs but a singular electrochemically-active material for the electrode, regardless of the physical state or configuration thereof. Of course, for the iontophoretic administration of certain of the medicaments within the scope of the present invention, particularly those not heretofore iontophoretically administered (especially proteinaceous and protein/metallic medicaments), a conventional galvanic couple might be employed. However, in selection of the appropriate materials for the couple, the skilled artisan will readily appreciate that less active metallic components than utilized in prior art devices may well be chosen due to the augmentive nature of the instant bandage respecting the inherent electrical characteristics of the mammalian body to which the bandage will be applied.

The most preferred electrode is a foil of aluminum metal. Other electrode materials include, for example, cooper, zinc, tin, and titanium, each of which will provide an effective positive charge with respect to the mammalian body. Should the medicament utilized require anet negative charge to provide the desired iontophoretic impetus of proper polarity, such materials as tantalum might be utilized.

Regardless of the electrode material or configuration thereof, it is essential that the electrode be in electrically cooperative relationship with the medicament to be iontophoretically administered. As a consequence, when the bandage is activated by electrolytic fluids such as, for example, body fluids or administered isotonic saline, voltaic interaction will establish an electric field between the electrode and underlying wound site and generate a corresponding electric current, whereby the medicament is caused to migrate deeply within the wound in response thereto.

Figure 2:
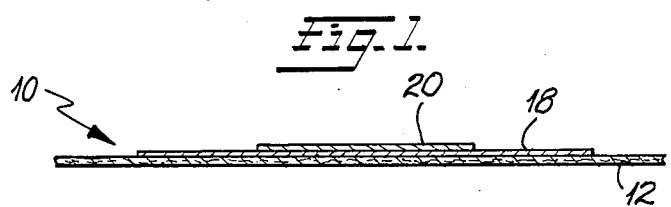
FIG. 2 is a cross-sectional view of the bandage of FIG. 1, taken substantially along line 2—2 thereof.

Referring to the Figures of Drawing, FIGS. 1 and 2 illustrate one embodiment of the bandage in accordance with the present invention. As used herein, and in the claims, the term bandage is meant to include all varieties of surgical dressings or plasters, regardless of physical configuration or dimensions, which may be applied over a wound site to effect treatment therefor. Thus, the present invention envisions utility extending from small adhesive bandages to large dressing of several square feet which may be applied to, for example, burn victims. The bandage of FIG. 1, denoted generally as 10, is comprised of, e.g., a 6"×2" substrate 12 having a medial portion 14 and terminal portions 16. The medial portion 14 has adhered thereto a foil of, for example, aluminum metal, denoted as 18. The foil, as illustrated in FIGS. 1 and 2, comprises approximately one half of the total surface area of the bandage substrate 12. However, these dimensions are not critical provided the electrode material has sufficient surface area to provide the required iontophoretic-effective electric current.

The central portion of electrode 18 has coated thereon, or adhered thereto, a quantity of the desired medicament 20. Preferably, the medicament is applied as a paste or liquid to some absorbent material such as tissue paper or sterile cloth or gauze. The medicament is allowed to dry and the porous carrier adhered to the foil electrode.

Figure 3:
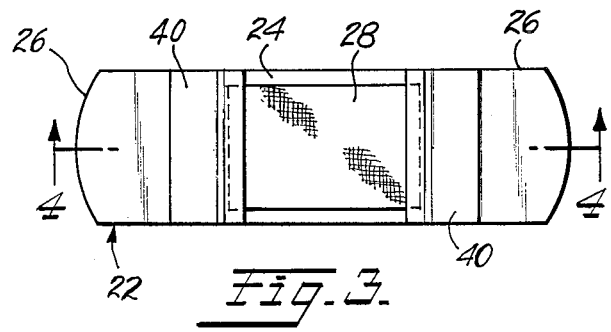
FIG. 3 is a plan view, similar to FIG. 1, showing an alternate bandage in accordance with the present invention; and, FIG. 4 is a cross-sectional view of the bandage of FIG. 3, taken substantially along line 4—4 thereof.
Figure 4:
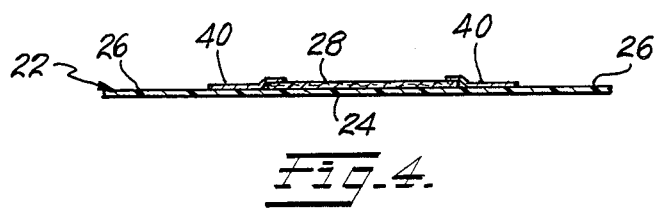

FIGS. 3 and 4 illustrate an alternate embodiment of the present invention, which employs a commercially available surgical bandage, such as those marketed under the trademark "CURAD". As opposed to the bandage of FIGS. 1 and 2, which may be made in relatively large dimensions, and wherein the terminal portions 16 may or may not be coated with an adhesive substance, the laternate embodiment of FIGS. 3 and 4 is designed for application to rather small cuts, abrasions or the like. The bandage is comprised of a plastic or polymeric substrate 22 having a medial portion 24 and adhesively coated end portions 26. An absorbent gauze 28 is adhered to the substrate 24 in the medial portion 24. Two foil electrode 40 are also borne upon substrate 22 and are caused to partially overlap the medial gauze area 28. The desired medicament may be applied to the gauze pad 28 and allowed to dry.

A bandage in accordance with the embodiment illustrated in FIGS. 3 and 4 was prepared in order to ascertain the effectiveness of the iontophoretic administration of mild silver protein to a human body. The bandage employed is approximately 7.5 cm long and 2.5 cm wide. The gauze pad 28 accounts for approximately 30% of the total surface area of the bandage and is coated with a solution of mild silver protein (USP) made isotonic with 0.9% sodium chloride. After the medicament has dried, two rectangular strips of aluminum foil having dimensions of about 2.5 cm×2.0 cm are adhered to the bandage substrate as shown in FIG. 3, partially overlapping the coated gauze area 28 such the approximately 15% of each aluminum foil strp is in direct contact with the coated gauze pad.

This bandage was placed on a human body over a minor wound. A drop of isotonic saline was administered to the coated gauze pad in order to establish voltaic action between the aluminum foil electrodes and the body. The electric potential was measured to be about $\frac{3}{4}$ of a volt, and the current generated about 10 microamperes. In response to the electric field thus generated, the silver protein medicament migrated deeply within the wound at a rate much greater than were the electric field absent.

A similar bandage was prepared, but in accordance with the embodiment of FIGS. 1 and 2. As a substrate, a commercially available bandage, marketed under the name "Air-Vent Tape Clear[, by Johnson & Johnson, was utilized. This bandage, measuring about 9.0 cm×2.6 cm, was placed with the adhesive side up, upon which was adhered, in the central portion thereof, a foil of aluminum metal measuring about 4.5 cm×2.0 cm×0.0254 mm. The adhesive of the bandage provided sufficent area for firm attachment of the foil thereto, leaving a small peripheral strip of adhesive exposed along the longitudinal edges of the foil due to its narrower transverse dimension relative to that of the bandage.

Sterile tissue paper, measuring 2.4 cm×2.4 cm, was soaked in a 10% solution of mild silver protein made isotonic with 0.9% sodium chloride. The tissue was removed from this solution and permitted to dry. Subsequently, the impregnated tissue was placed over the aluminum foil, the exposed adhesive from the bandage providing means for firm attachment.

This bandage was applied over a cut on a human body, perspiration and wound serum providing the requisite poly electrolyte. The voltage of the resultant electric field was measured at about 1 volt; the current varied between 5 and 15 microamperes as the iontophoretic process proceeded to carry the medicament deeply within the wound.

Depending upon the configuration of the electrodes, and their relative placement with respect to the medicament coating, various bandages have been tested and have been found to develop between about $\frac{1}{2}$ and 1 volt potential, and between about 2 and about 15 microamperes current, for aluminum foil electrodes. Obviously, various other electrode materials will provide differing electrical characteristics.

Yet another embodiment envisioned within the scope of the present invention regards the use of soft, hydrogel materials, such as those disclosed in, for example, U.S. Pat. Nos. 2,976,576, Re. 27,401, 220,960, 3,503,942, 3,639,524, 3,699,089, 3,721,657 and 3,966,847. These materials, which will swell and retain, by hydration, solutions of the desired medicaments, may be employed as carriers therefor in lieu of the saturated tissue or sterile gauze materials. Otherwise, the bandage is identical in all respects to those enumerated above.

From the foregoing descriptions, it is apparent that the bandage of the present invention is very versatile, and may be readily tailored for a wide range of applications as the circumstances might dictate in any given situation. Thus, the size and shape of the bandage substrate, which may or may not be provided with an adhesive, may be suitably adjusted depending upon type and location of the wound to be treated. Similarly, the variety of electro-chemically-active materials employed as the electrode, and its physical configuration, as well as the particular medicament may be altered for specific applications, all of the foregoing parameters capable of appropriate selection by the skilled artisan.

While the invention has now been described in terms of certain preferred embodiments, and exemplified with respect thereto, the skilled artisan will appreciate that various other modifications, changes, substitutions, and omissions may be made without departing from the spirit thereof. Accordingly, it is intended that the scope of the present invention be limited solely by that of the following claims.

What is claimed is:

1. A bandage for iontophoretically administering a topical or systemic ionizable or polar medicament to a mammalian body having a wound, lesion, or the like thereon, comprising:
   (a) a substrate
   (b) an ionizable or polar medicament borne on said substrate, which medicament is responsive, in terms of migration to an electric field; and
   (c) a single electrode of an electrochemically-active material in electrically cooperative relationship with said medicament, for generating an iontophoretically effective, localized electric current between said medicament and the mammalian body to which the bandage is applied, to thereby cause the medicament to migrate deeply within said wound, lesion, or the like upon activation of the bandage by electrolytic fluids.

2. The bandage of claim 1, wherein said substrate defines a medial portion bounded by terminal portions, said electrode borne upon said substrate within said medial portion and supporting a discrete quantity of said medicament within its peripheral dimensions, said electrode presenting sufficient surface area for contact with said body to establish an iontophoretically-effective electric current between said medicament and said body to cause migration of said medicament deeply within said wound, lesion, or the like thereon.

3. The bandage of claim 1, wherein said substrate defines a medial portion bounded by terminal portions, said medicament borne upon said substrate within said medial portion, said electrode being confined to at least one of said terminal portions and partially overlapping said medial portion in electrically-cooperative relationship with said medicament.

4. The bandage of claim 1, wherein said medicament is absorbed within a carrier selected from the group consisting of sterile paper, sterile cloth, and hydrogel polymers, said carrier being adhered to said bandage.

5. The bandage of claim 1, wherein said medicament is a proteinaceous medicament.

6. The bandage of claim 5, wherein said proteinaceous medicament is comprised of an undenatured protein.

7. The bandage of claim 5, wherein said proteinaceous medicament is comprised of a denatured protein.

8. The bandage of claim 7, wherein said proteinaceous medicament further comprises a bio-compatible metallic medicament.

9. The bandage of claim 8, wherein the metal is silver.

10. The bandage of claim 5, wherein said medicament is silver protein.

11. The bandage of claim 10, wherein said electrode is aluminum metal.

12. The bandage of claim 11, wherein said aluminum is applied as either a foil or as a paint.

13. A method for iontophoretically administering a topical or systemic ionizable or polar medicament to a mammalian body having a wound, lesion, or the like thereon, whereby said medicament is responsive, in terms of migration, to an electric field, comprising the step of generating an electric field by voltaic interaction between a single electrode of electrochemically-active material borne upon a bandage substrate and in electrically-cooperative relationship with said medicament, and said body when said bandage substrate is placed over said wound, lesion, or the like, upon activation of the bandage by electrolytic fluids, whereby the medicament is caused to migrate deeply within said wound, lesion, or the like.

14. The method of claim 13, wherein said medicament is a proteinaceous medicament.

15. The method of claim 14, wherein said proteinaceous medicament is comprised of an undenatured protein.

16. The method of claim 14, wherein said proteinaceous medicament is comprised of a denatured protein.

17. The method of claim 16, wherein said proteinaceous medicament further comprises a bio-compatible metallic medicament.

18. The method of claim 17, wherein the metal is silver.

19. The method of claim 14, wherein said medicament is silver protein and said electrode is a metal foil capable of establishing a net positive electric charge with respect to said body.

20. The method of iontophoretically adminstering an ionizable or polar medicament as defined by claim 13, wherein said medicament is in a dry state, said method further comprising the step of hydrating said medicament with an electrolyte fluid.

21. The method of claim 20, wherein said electrolyte fluid is either the fluid within the wound, lesion, or the like or is isotonic saline.

22. The method of claim 20, wherein said electrode is aluminum foil.

* * * * *